United States Patent [19]

Phuc

[11] Patent Number: 4,543,951

[45] Date of Patent: Oct. 1, 1985

[54] RESPIRATOR WITH TWO JET GAS INJECTION TUBES

[75] Inventor: Tran N. Phuc, Ohmiya, Japan

[73] Assignee: Senko Medical Instrument Mfg. Co., Ltd., Tokyo, Japan

[21] Appl. No.: 477,522

[22] Filed: Mar. 21, 1983

[30] Foreign Application Priority Data

Nov. 30, 1982 [JP] Japan .................... 57-209948

[51] Int. Cl.[4] ............................................. A61M 16/00
[52] U.S. Cl. ........................ 128/204.25; 128/911; 128/205.19; 128/910
[58] Field of Search ............... 128/204.25, 204.18, 128/205.19, 207.14, 207.15, 207.16, 204.21, 204.23, 910, 911, 204.24, 205.24

[56] References Cited

U.S. PATENT DOCUMENTS

| | | | |
|---|---|---|---|
| 2,787,999 | 4/1957 | Bennett | 128/205.23 |
| 2,904,033 | 9/1959 | Shane | 128/205.23 |
| 3,485,243 | 12/1969 | Bird et al. | 128/204.25 |
| 3,923,055 | 12/1975 | Hammacher | 128/204.23 |
| 3,993,059 | 11/1976 | Sjostrand | 128/205.13 |
| 4,265,237 | 5/1981 | Schwanbom et al. | 128/204.24 |
| 4,270,530 | 6/1981 | Baum et al. | 128/204.25 |
| 4,281,652 | 8/1981 | Miller | 128/911 |
| 4,363,238 | 12/1982 | William | 128/725 |
| 4,463,755 | 8/1984 | Suzuki | 128/911 |
| 4,463,756 | 8/1984 | Thuc | 128/204.21 |

FOREIGN PATENT DOCUMENTS

| | | | |
|---|---|---|---|
| 0047185 | 3/1982 | European Pat. Off. | 128/205.24 |
| 8203014 | 9/1982 | European Pat. Off. | 128/207.15 |

*Primary Examiner*—Henry J. Recla
*Attorney, Agent, or Firm*—Cushman, Darby & Cushman

[57] ABSTRACT

An artificial respirator of a high-frequency oscillation ventilation type is provided which is free from a risk of increasing pressure in the airways. The respirator comprises a double communication tube with inner and outer tubes. One of the tubes is utilized for feeding a respiration or anesthetic gas to the airways through an endotracheal cannula, and the other tube is connected to a communication tube in which two jet air injection tubes are provided. The first jet air injection tube is utilized for injecting a jet respiration gas to thereby transmitting high-frequency oscillations to the respiration or anesthetic gas. The second jet air injection tube is utilized for injecting a jet respiration gas toward outside of the communication tube from therewithin thereby to decrease the pressure in the communication tube and hence in the airways.

6 Claims, 3 Drawing Figures

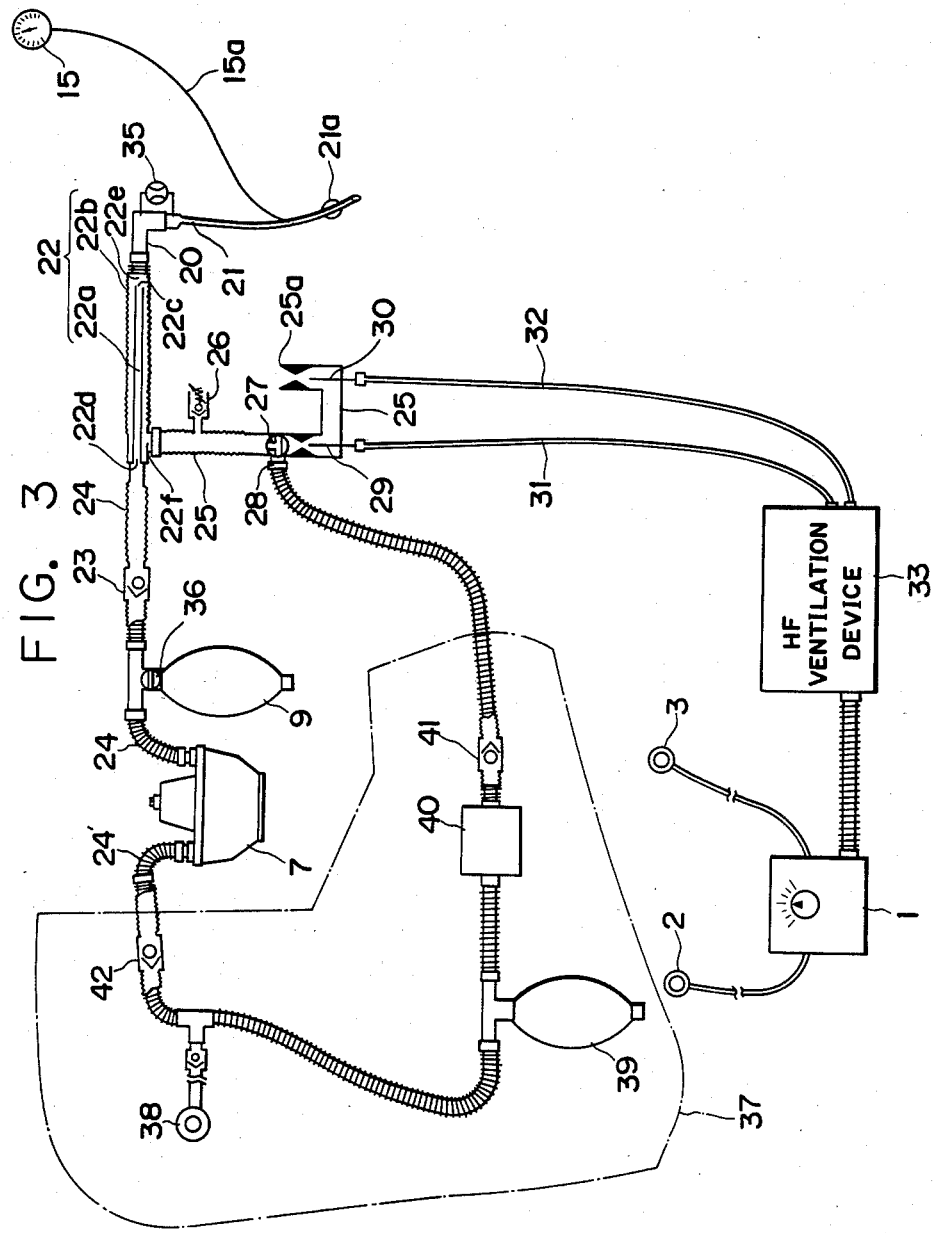

4,543,951

RESPIRATOR WITH TWO JET GAS INJECTION TUBES

BACKGROUND OF THE INVENTION (1) Field of the Invention

This invention relates to an artificial respirator with two jet gas injection tubes which can afford a high efficiency of ventilation by high-frequency oscillation.

(2) Description of the Prior Art

As is well known, natural respiration or breathing is effected by inflating the lungs to maintain the pressure in the trachea and bronchi at a negative pressure to inspire air and by deflating the lungs to maintain the pressure in the trachea and bronchi at a positive pressure. Recently, a new artificial respiration method has been proposed and widely used in the medical fields. This method is referred to as a high-frequency oscillation (HFO) ventilation method in which a jet gas of auxiliary respiration gas is injected into the trachea and bronchi at a relatively high repetition frequency of 200 to 5000 cycles per minute so that the respiration gas in the lungs is stirred up to enhance the ventilation. Thus, the partial pressures of $O_2$ and $CO_2$ in the blood are kept to a proper level even during apnea.

One previously known such a respirator is shown illustratively in FIG. 1. In the figure, a respiration gas is generated in a gas mixer 1, gas sources 2 and 3 of oxygen and air being respectively coupled for feeding the gasses thereto. A proper amount of oxygen and air is introduced into the mixer 1 and then is mixed to produce a mixture gas for use in respiration.

The respiration gas thus produced is delivered through a communication tube 6 to a humidifier 7 where the respiration gas is made humid. After being humidified, the respiration gas is supplied through a communication tube 8 and further through an endotracheal cannula 11 into the lungs. The cannula 11 is coupled to the tube 8 by means of a T-fitting 10 at its one opening. In the midst of the path along the communication tube 8, a rebreathing bag 9 is provided so as to accumulate the respiration gas therein for supplying, when occasion demands, an additional gas to the lungs by squeezing it. The remaining opening of the T-fitting 10 opens into air by way of a communication tube 12 having a predetermined length. The tube 12 functions to impart resistance against the gas flow and hence to impart a small positive pressure to the respiration gas for use in the ventilation. In addition, the tube 12 is also used for the passage of the gas expiring from the lungs through the cannula 11 into air. At the vicinity of the cannula end, a cuff 11a is provided for blocking the intermediate flow passage between the airways and the outer surface of the cannula 11, thereby preventing a leakage of the respiration gas within the airways into air. However, it is not necessary to have the cuff 11a so long as a high-frequency oscillation method is employed because there is no substantial leakage of the respiration gas in such a method. In this case. the expired gas from the lungs can be expelled out into air through the intermediate passage and also through the cannula 11a and tube 12.

The respiration gas in the mixer 1 is also delivered to a high-frequency ventilation device 5 which is composed of a pneumatic circuit comprising fluidic devices. The fluidic devices operate to change the flow lines of the gas circuit in response to variations in the pressure of the gas. The gas thus controlled is transformed into a jet air having predetermined volume and high repetition frequency, e.g., 200 to 5000 cycles per minute. The jet gas is thereafter guided through a gas tube 13 into a jet gas injection tube 14 with a small diameter of about 1 mm, the tip of the injection tube 14 being inserted into the interior of the cannula 11 for feeding the jet gas thereinto.

The respiration gas to be transported through the humidifier 7, the rebreathing bag 9, and the T-fitting 10 into the lungs is subjected to high-frequency oscillations due to the presence of the jet gas. Therefore, an improved ventilation, commonly called as ventilation by high-frequency oscillations, can be performed effectively. In order to monitor the internal pressure in the airways and to prevent risk of a possible high pressure, a pressure gauge 15 is used, and its measuring guide tube 15a is inserted into the cannula 11 at the location downstream from the opening end of the jet gas injection tube 14.

The respirator of this design described above has been found not entirely satisfactory, however, and has many disadvantages as in the following;

(1) A sufficient supply of the respiration gas into the lungs can be retained by virtue of the injection of the jet gas from the injection tube 14. While on the other hand, since the expired gas from the lungs are left as it is without taking any positive measures to forcibly expel it out of the lungs, through the cannula 11 and the tube 12, the expired gas in the airways is liable to halt and linger within the airways. As a result, the increase of the internal pressure of the airways most likely occurs with the lapse of time, and there is a fear for effecting adverse effects upon a patient under artificial ventilation.

(2) The position where the internal pressure is measured is located at the vicinity of the downstream of the jet gas from the injection tube 14 so that a correct or practically useful pressure can not be obtained.

(3) A relatively large volume of the jet gas with a high pressure is supplied from the jet gas injection tube 14 during ventilation, so that it is very hard to humidify and heat the respiration gas as desired, particularly when the ventilation is carried out for a long time duration.

(4) Furthermore, anesthetic material can not be vaporized with a precise density if the vaporization is carried out under a high flow rate of more than 20 liters per minute and high pressure of 0.1 to 5 kg per $cm^2$, of the respiration gas. This brings about a hardship that an anesthetic apparatus can not be easily equipped with the respirator. It is not practical for the respirator to prepare and implement additional complicated circuits enabling the attachement of the anesthetic apparatus to the respirator.

SUMMARY OF THE INVENTION

Therefore, it is a primary object of the invention to provide a novel respirator which is free from a risk of increasing pressure in the airways.

It is another object of the invention to provide the respirator as above in which the pressure in the airways as well as the flow rate of a respiration or anesthetic gas into the airways can be correctly and precisely measured.

It is further object of the present invention to provide the respirator as above in which an anesthetic apparatus can be readily equipped therewith without employing additional complicated circulation circuits for anesthesia. In addition to the above effect, the anesthetic apparatus, when applied to the respirator according to the invention, can operate with a high anesthetic efficiency and is capable of easy humidification and heating of an anesthetic gas.

In a preferred example of the present invention which will be described hereinunder in detail, the respirator comprises:

a double tube with inner and outer tubes disposed in a substantially concentric arrangement with each other, said inner tube having first and second openings at opposite ends thereof with respect to its longitudinal direction and said outer tube having third and fourth openings, said third opening being formed at one end thereof with respect to its longitudinal direction and said fourth opening being formed in the wall of the outer tube at the vicinity of the other end thereof, wherein said first opening opens into said outer tube at the vicinity of said third opening and the periphery of said second opening is formed integral with the other end of said outer tube;

an endotracheal cannula coupled to said double tube through said third opening;

a first communication tube coupled to said double tube through said second opening for feeding a respiration gas to be supplied from a gas source to said endotracheal cannula through said outer tube;

a second communication tube coupled at one end thereof to said double tube through said fourth opening and opening into air at the other end thereof, said second tube being mounted with first and second jet gas injection tubes positioned at the vicinity of said other end, said first injection tube being directed toward said one end of said second communication tube and said second injection tube being directed toward said the other end of said second communication tube; and a ventilation device coupled to said first and second injection tubes for feeding said respiration gas alternately and intermittently to said first and second injection tubes, whereby said respiration gas is transformed into a jet stream.

The foregoing and other objects, the features and the advantages of the present invention will be pointed out in, or apparent from, the following description of the preferred embodiments considered together with the accompanying drawings.

BRIEF DESCRIPTION OF THE DRAWINGS

FIG. 3 is a diagrammatic illustration in which an anesthetic apparatus is applied to the respirator shown in FIG. 2

DETAILED DESCRIPTION OF THE PREFERRED EMBODIMENTS

Figure 1:
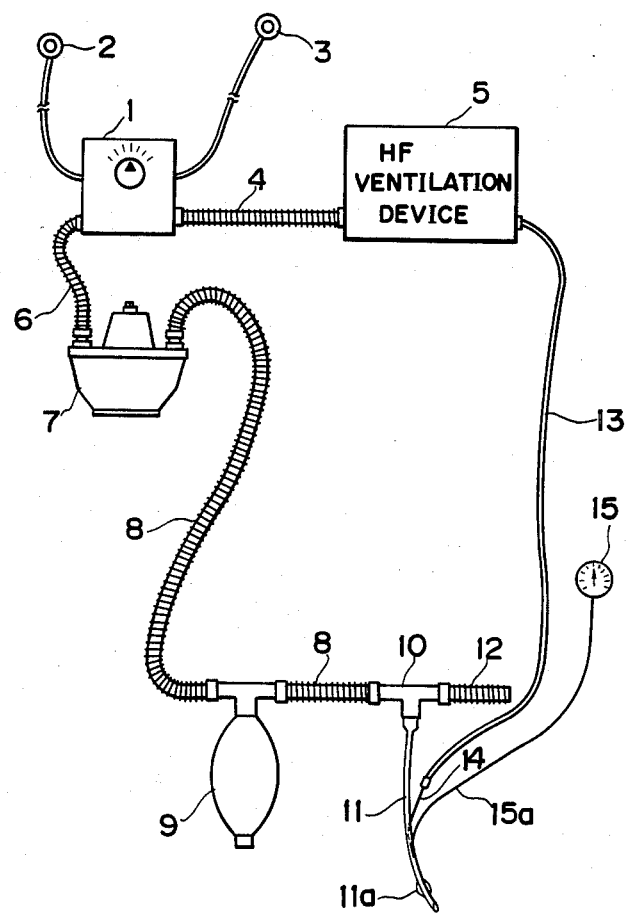
FIG. 1 is a diagrammatic illustration of a prior art respirator of a high-frequency oscillation ventilation type.
Figure 2:
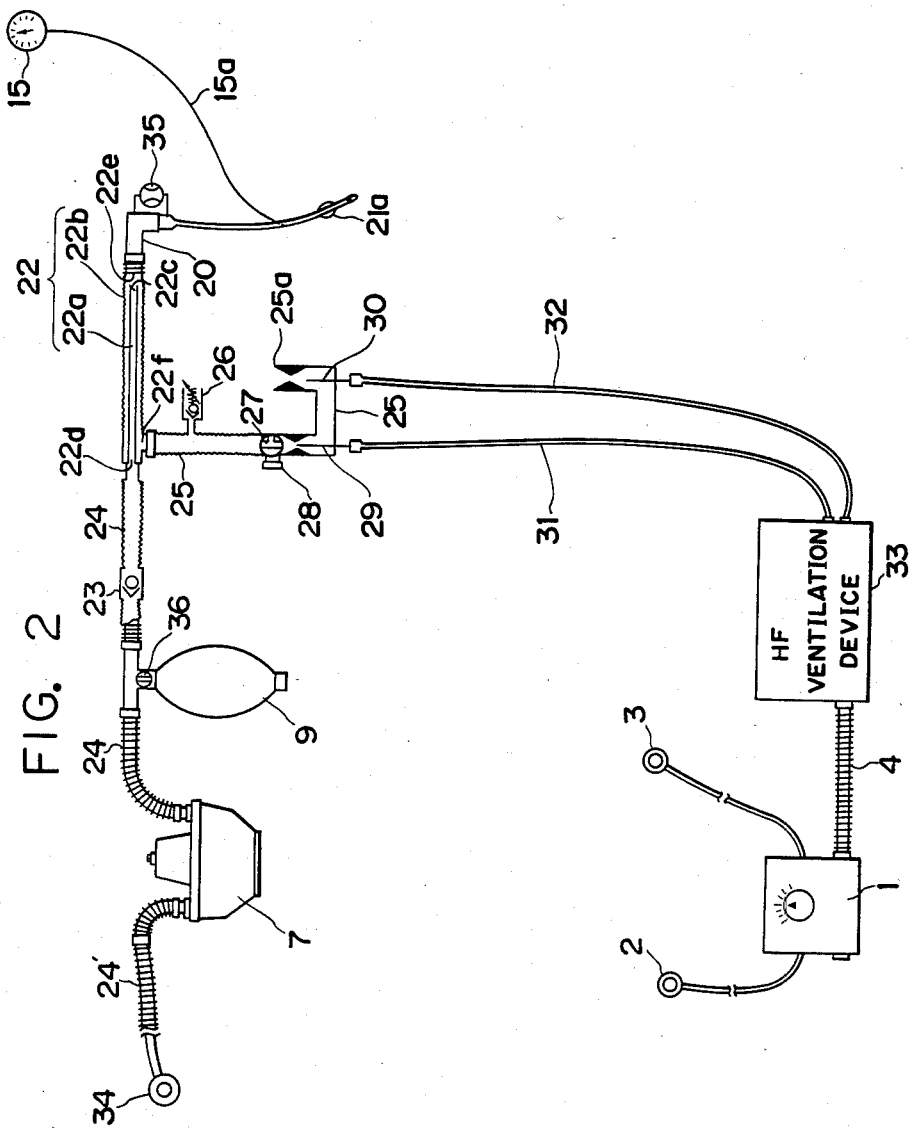
FIG. 2 is a diagrammatic illustration of the respirator with two jet air injection tubes according to the invention.

The invention will now be described with reference to the accompanying drawings. FIG. 2 shows a first embodiment according to the invention. In the figure, identical reference numbers have been used for indicating parts and components similar to those in FIG. 1, and the description thereof has been omitted for the purpose of brevity. In this embodiment, an endotracheal cannula 21 similar in construction as of the cannula 11 of FIG. 1 is employed. A cuff 21a and a pressure gauge 15 are also provided, the former, which can be dispensed with as described previously, being mounted at the vicinity of the cannula 21, and the latter being associated with the cannula 21 by inserting therein the opening end of a measuring tube 15a. The cannula 21 is coupled to one opening of a L-fitting 20 for communicating therethrough with a double communication tube 22 which is coupled to the other opening of the L-fitting 20. The double communicating tube 22 has two passageways, i.e., a first communication tube 22a constructed as an inner tube and a second communication tube 22b constructed as an outer tube. The outer tube 22b may preferably be made of material flexible in nature. One of the openings 22e of the outer tube 22b is formed in a shape to facilitate the coupling to the L-fitting, while the other opening 22f is formed at the outer surface thereof adjacent to the end opposite to the opening 22e. One of the openings 22c of the inner tube 22a opens into the outer tube 22b at the vicinity of the one opening 22e of the tube 22b, while the other opening 22d is made integral with the outer tube 22a at the end thereof opposite to the opening 22e.

A humidifier 7, a rebreathing bag 9, and a check valve 23 are coupled in this order by means of a communication tube 24 to the opening 22d of the inner tube 22a of the double communication tube 22, the check valve 23 functioning to allow the respiration gas to move only in a direction toward the double tube 22.

The second or outer tube 22b is coupled at the opening 22f to a second communication tube 25, the tube 25 being provided with a pop-off valve 26 nearer to the opening 22f and a three-way valve 27 remoter from the opening 22f. The pop-off valve 26 aims at lowering the pressure in the tube 25 when it goes higher than a predetermined pressure. A port 28 is formed at the outside of the tube 25 which opens into air and can be used to cause the flow passage of the tube 25 communicable with an anesthetic circuit described later in cooperation with the three-way valve 27.

A pair of first and second jet gas injection tubes, respectively made of a capillary tube having a diammeter of about 1 mm, are inserted into and fixed at the extremity of the tube 25 remotest from the opening 22f. The former tube is directed toward the three-way valve 27, and the latter tube is directed toward an open end 25a. The inside of the tube 25 where the first and second injection tubes 29 and 30 are located are respectively made narrower in order to enhance the exhale of the jet gas out of the capillary tubes 29 and 30 and the inhale of the jet gas into the tube 25 or into air, by virtue of a pressure reducing effect.

The injection tubes 29 and 30 are coupled through gas tubes 31 and 32 to a high-frequency ventillation device 33 which is similar in construction as that of the device 5 in FIG. 1. A respiration gas to be supplied to the device 33 is given through a communication tube 4 from a mixer 1 of a similar kind as of FIG. 1, oxygen and air being fed from suitable gas sources 2 and 3 to the mixer 1.

The ventilation device 33 is constructed in such a way that a respiration gas is alternately supplied to the first and second injection tubes 29 and 30 with a high repetition frequency of 200 to 5000 cycles per minute, and that the pressure of a respiration gas can be changed independently of one another. Thus, after a respiration gas having a desired pressure is supplied to the tube 29 during a certain period, then a respiration gas with another desired pressure is this time supplied to the second tube 30, and thereafter this process is repeated successively one after another.

The humidifier 7 is provided with another communication tube 24' with an intake port 34 through which a respiration gas is supplied from the mixer 1 or another suitable respiration gas source (not shown). However, in the case when thus constructed respirator is utilized for anesthetic application, an anesthetic gas is introduced through the intake port 34 into the humidifier 7.

In the above embodiment, it may be preferable to mount a flow meter 35 at the L-fitting 20 and to mount a two-way valve 36 at the neck of the rebreathing bag 9.

Next, the operation of the respirator with two jet gas injection tubes according to the invention will be described in detail.

A respiration gas is first introduced through the intake port 34 into the humidifier 7 wherein moderate moisture is imparted to the respiration gas. The humidified respiration gas is then transported through the rebreathing bag 9, check valve 23, and first or inner tube 22a into the airways of a patient. Upon activation of the high-frequency ventilation device 33, a respiration gas in a jet state is delivered alternately and intermittently to one of the capillary tubes 29 and 30 with a high repetition frequency.

During the time a jet gas is delivered to the capillary tube 29, the respiration gas having been supplied from the inner tube 22a and filled up within the airways is subjected to high oscillations of the jet gas which is transmitted through the tube 25 and outer tube 22b, thereby promoting ventilation to a large extent.

During the time the deliverance of the jet gas to the capillary tube 29 is stopped and being directed in turn to the capillary tube 30, the pressure in the vicinity of the open end 25a is decreased due to the jet gas. Accordingly, the gas pressure in the tube 25 and outer tube 22b is also lowered so that the expired air from the lungs can be smoothly expelled to the ambient surroundings through the open end 25a.

In addition to the improvements of ventilation thus obtained, a more correct and precise pressure of the airways can be measured by means of the pressure gauge 15. This is because the position of the tip of the tube 15a is located nearer to the airways and hence to the lungs, and is located remoter from the tip of the jet gas tube 29, when compared with the conventional arrangement. It is also true in the same sense in the case of the flow meter 35 which is located nearer to the lungs.

Apart from the aforementioned advantages, the respirator according to the invention can meets various requirements of the patient at a time. More in particular, since the jet gas pressure supplied to the first and second tubes 29 and 30 can be independently adjusted by the ventilation device 33, positive and negative peak pressures of the respiration gas can be separately determined in compliance with the patient conditions.

This respirator can also be used as an anesthetic apparatus simply by supplying anesthetic gas in stead of the respiration gas to the intake port 34. In this case, since the opening 22c of the inner tube 22a is located away from the tip of the injection tube 29, only a small amount of the jet respiration gas is mixed into the anesthetic gas and the dilution of the respiration gas is maintained small. Therefore, it is appreciated that owing to the low dilution and high-frequency oscillations as well, a small amount of dosage of anesthetic gas may suffice for the patient, e.g., for an adult 5 to 6 liters per minute. Further, it is easy to humidify and heat the anesthetic gas.

FIG. 3 shows a second embodiment of the respirator according to the invention, wherein identical reference numbers have been used for indicating similar components to those in FIG. 2 and the description thereof has been omitted. This embodiment can be used both as a respirator and as an anesthetic apparatus by changing over the three-way valve 27.

An anesthetic circuit 37 of a known circulation type is coupled between the port 28 and the connection tube 24'. The circuit 27, as shown in FIG. 3, comprises an auxiliary bag 39 for delivering auxiliary anesthetic gas to the patient by squeezing it, a carbon dioxide adsorber 40 for removing carbon dioxide gas contained in the circulating anesthetic gas, and check valves 41 and 42 for allowing the gas to pass toward and from the patient, respectively. The anesthetic gas is supplied from the anesthetic gas source via an intake port 38 coupled between the valve 42 and the bag 39.

In operation, while the three-way valve 27 is turned to the anesthetic circuit 27, a known circulation type anesthesia is performed with the two-way valve 36 closed. If an ordinary artificial ventilation is required, then the valve 27 is turned to the ventilation device 33 in order to communicate the capillary tube 29 with the tube 25 and to close the passage toward the anesthetic circuit 37. It is to be understood here that, by virtue of a high efficiency of high-frequency oscillation ventilation, it may be possible to supply the respiration gas only from the capillary tube 29 without further supplying it from the inner tube 22a as described in the first embodiment. Thus, the respirator according to the second embodiment can quickly deal with both anesthesia and ventilation and can meet any changes of the patient. This is particulary useful for the patient under a long time operation.

What is claimed is:

1. A high-frequency respirator comprising;
    a double tube with inner and outer tubes disposed in a substantially concentric arrangement with each other, said inner tube having first and second openings at opposite ends thereof with respect to its longitudinal direction and said outer tube having third and fourth openings, said third opening being formed at one end thereof with respect to its longitudinal direction and said fourth opening being formed in the wall of the outer tube at the vicinity of the other end thereof, wherein said first opening opens into said outer tube at the vicinity of said third opening and the periphery of said second opening is formed integral with the other end of said outer tube;
    an endotracheal cannula coupled to said double tube through said third opening;
    first communication tube means coupled to said double tube through said second opening for feeding a respiration gas to be supplied from a gas source to said endotracheal cannula through said inner tube;
    second communication tube means coupled at one end thereof to said double tube through said fourth opening and opening into air at the other end thereof, said second communication tube means being mounted with first and second jet gas injection tubes positioned at the vicinity of said other end, said first injection tube being directed toward said one end of said second communication tube means and said second injection tube being directed toward said the other end of said second communication tube means; and high-frequency ventilation means having first and second outlet ports for alternately and intermittently outputting therefrom a gas at a frequency of 200 to 5000 cycles per minute, said first and second outlet ports being connected to said first and second injection tubes, respectively, so that said gas outputted from the ventilation means is transformed into a jet stream which causes said respiration gas, introduced into said endotracheal cannula through said inner tube, to oscillate.

2. A respirator as claimed in claim 1, wherein said second communication tube means further includes (a) an outlet port on a wall thereof at a location nearer to said one end with respect to said first and second injection tubes, (b) means defining first and second passageways said first passageway permitting communication between said one end and said outlet port and preventing communication between said one end and said first injection tube, and said second passageway permitting communication between said one end and said first injection tube and preventing communication between said outlet port and said first injection tube, and (c) changeover means for selecting either one of said first and second passageways, and wherein said respirator further comprises a circulation type anesthetic circuit including a source of anesthetic gas, said circuit coupled between said outlet port and said first communication tube, and wherein selection of said first passageway by said changeover means feeds an anesthetic gas supplied to said circuit from said source to said endotracheal cannula through said inner tube, and wherein selection of said second passageway by said changeover means establishes communication of said first injection tube withhid one end for feeding said respiration gas to said endotracheal cannula through said inner tube.

3. A respirator as claimed in claim 1, further comprising a pressure gauge including a measuring tip, said measuring tip being inserted within said endotracheal cannula.

4. A respirator as claimed in claim 2, further comprising a pressure gauge including a measuring tip, said measuring tip being inserted within said endotracheal cannula.

5. A respirator as claimed in claim 1 further comprising coupling means to be interposed between said endotracheal cannula and said double tube through said third opening, said coupling means being provided with a flowmeter for measuring the flow rate of a gas delivered to and from said endotracheal cannula.

6. A respirator as claimed in claim 2, further comprising coupling means to be interposed between said endotracheal cannula and said double tube through said third opening, said coupling means being provided with a flowmeter for measuring the flow rate of a gas delivered to and from said endotracheal cannula.

* * * * *